(12) United States Patent
Kalachev et al.

(10) Patent No.: US 8,357,896 B2
(45) Date of Patent: Jan. 22, 2013

(54) METHOD OF ANALYZING A SUBSTANCE

(75) Inventors: Alexey Kalachev, Berlin (DE); Jürgen P. Rabe, Berlin (DE); Nikolai Severin, Berlin (DE)

(73) Assignee: Humboldt-Universitat Zu Berlin, Berlin (DE)

( * ) Notice: Subject to any disclaimer, the term of this patent is extended or adjusted under 35 U.S.C. 154(b) by 0 days.

(21) Appl. No.: 13/044,459

(22) Filed: Mar. 9, 2011

(65) Prior Publication Data

US 2012/0228495 A1  Sep. 13, 2012

(51) Int. Cl.
*G01N 23/00* (2006.01)
*G21K 7/00* (2006.01)

(52) U.S. Cl. ............... 250/310; 250/306; 250/492.1; 250/251; 250/396 R; 252/500; 252/502; 435/7.1; 435/39

(58) Field of Classification Search ............ 250/306, 250/310, 492.1, 251, 396 R; 252/500, 502; 435/7.1, 39
See application file for complete search history.

(56) References Cited

U.S. PATENT DOCUMENTS

| | | | |
|---|---|---|---|
| 2007/0104860 A1* | 5/2007 | Gleason et al. | 427/2.14 |
| 2007/0218283 A1 | 9/2007 | Geng et al. | |
| 2009/0166560 A1* | 7/2009 | Dai et al. | 250/492.1 |
| 2010/0127312 A1 | 5/2010 | Grebel et al. | |
| 2010/0255984 A1 | 10/2010 | Sutter et al. | |
| 2012/0156688 A1* | 6/2012 | McAlpine et al. | 435/7.1 |

FOREIGN PATENT DOCUMENTS

WO  WO-2010/074918 A1  7/2010

OTHER PUBLICATIONS

Eberlein, T. et al. "Plasmon spectroscopy of free-standing graphene films", Physical Review, 2008, vol. 77, pp. 233406-1 to 233406-4.
Lee, C. et al. "Elastic and frictional properties of graphene", Phys. Status Solidi B, 2009, vol. 246, No. 11-12, pp. 2562-2567.
Lombardi, J. et al. "A Unified Approach to Surface-Enhanced Raman Spectroscopy", J. Phys. Chem. C, 2008, vol. 112, pp. 5605-5617.
Domke, Katrin F. and Bruno Pettinger, "Tip-Enhanced Raman Spectroscopy of 6H-SiC with Graphene Adlayers: Selective Suppression of E1 Modes," Journal of Raman Spectroscopy, 2009, vol. 40, pp. 1427-1433.
Kim, Nayoung et al., "Effect of Gold Substrates on the Raman Spectra of Graphene," Bull. Korean Chem. Soc., 2010, vol. 31, No. 4, pp. 999-1003.
Sutter, Eli et al., "Monolayer Graphene as Ultimate Chemical Passivation Layer for Arbitrarily Shaped Metal Surfaces," Carbon, 2010, vol. 48, pp. 4414-4420.
Notification of Transmittal of the International Search Report and the Written Opinion of the International Searching Authority, or the Declaration in PCT/EP2012/053562 dated Jun. 26, 2012.

* cited by examiner

*Primary Examiner* — Jack Berman
*Assistant Examiner* — Meenakshi Sahu
(74) *Attorney, Agent, or Firm* — Foley & Lardner LLP

(57) ABSTRACT

An embodiment of the invention relates to a method of analyzing a substance comprising the steps of: fabricating a structure comprising said substance and at least one graphene layer; carrying out at least one measurement step with respect to said structure; and analyzing the measurement result of said measurement step to receive at least one analytical result concerning said substance.

15 Claims, 3 Drawing Sheets

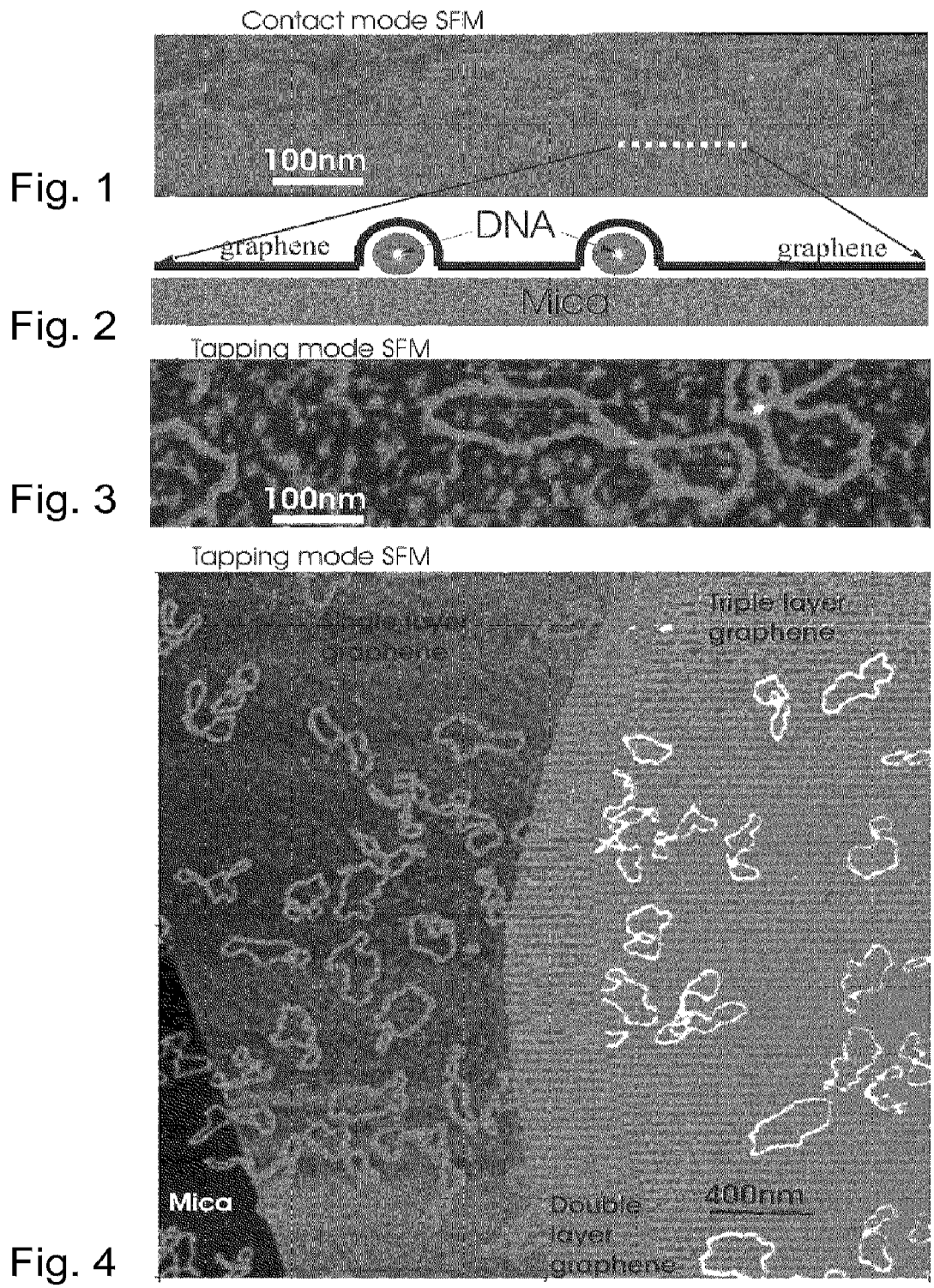

METHOD OF ANALYZING A SUBSTANCE

The present invention relates to a method of analyzing substances. More particularly, the invention relates to a method of analyzing substances of very small quantities.

BACKGROUND OF THE INVENTION

The analysis of single molecules or thin layers thereof is of both technological and scientific importance. There are a few methods which can unambiguously identify a-priori unknown little quantities of material down to single molecules. However, all these methods suffer from some shortcomings, and therefore have not been technologically implemented yet. General reasons are low sensitivities of the analytical methods and the instability of thin molecular layers and especially single molecules with respect to their thermal, chemical and photo-degradation or to external mechanical fields caused, e.g., by scanning probe microscopy (SPM) tips. Therefore it would be advantageous to improve these methods.

A few modifications of Surface Enhanced Raman Spectroscopy (SERS) can provide Raman spectra of small molecular quantities down to single molecules. A Raman spectrum is a "fingerprint" of a molecule. However, without surface enhancement the probability for a photon to be Raman scattered is very low, such that only large material quantities can be analyzed. On the one hand SERS is based on electromagnetic field enhancement by nano-structures made of plasmon active materials, and on the other hand on some chemical interaction between the surface and the molecule. A surface roughened in a certain manner has a few "active" sites, which enhance the Raman signal substantially to detect it even from single molecules located at the sites. One of the disadvantages of the above described method is the random nature of the active sites. One cannot analyze any molecule at will, since the active sites are usually not precisely known, and, e.g., the molecules have to interact in a particular way with the active sites. The above-mentioned disadvantage can be overcome by precisely fabricated nano-structures. Modern lithography methods do not allow, however, building highly efficient nano-structures reproducibly, since efficient field enhancement requires nanometer precision, which cannot be provided by, e.g., electron beam lithography.

A further disadvantage of prior art SERS is the strong difference between the Raman spectra in solution and the SERS Raman spectra, which are attributed, to some extent, to a specific chemical interaction between the molecule and the SERS active material. Also the molecules have to be placed precisely into the nano-structures to be analyzed.

The above-mentioned disadvantages may be overcome to some extent by the so called Tip Enhanced Raman Spectroscopy (TERS). TERS employs a sharp tip made of a plasmon active material. The tip is placed over an area of interest and enhances Raman scattering of molecules located in the nearest proximity to the tip apex. TERS has its own difficulties: one has to position the tip with high precision in order not to damage the molecules on the surface.

Similarly to TERS and SERS, also infrared spectra of molecules can be enhanced with plasmon active structures. The enhancement is not as strong as for Raman spectroscopy in the visible range, and a single molecule analysis is yet to be demonstrated.

A common disadvantage of all the above-described methods is the large amount of heat produced by the focused plasmon localized at the active site, i.e. high temperatures can cause oxidative damage to the molecules.

OBJECTIVE OF THE PRESENT INVENTION

An objective of the present invention is to provide a method which allows analyzing substances with very accurate results.

BRIEF SUMMARY OF THE INVENTION

An embodiment of the invention relates to a method of analyzing a substance comprising the steps of: fabricating a structure comprising said substance and at least one graphene layer; carrying out at least one measurement step with respect to said structure, and analyzing the measurement result of said measurement step to receive at least one analytical result concerning said substance.

On the one hand graphene is a monoatomically thick flexible and both electrically and thermally conductive layer of carbon atoms, and on the other hand it is optically transparent, impermeable to gases and liquids, and on solid substrates it protects against wear. Thus graphene can act as an optically transparent surface protective layer against local heating, wear and interactions with the ambient environment. Moreover, graphene exhibits its own plasmon resonance at ultraviolet wavelengths with a tail into the blue spectral region.

Preferably, at least one bent surface section is fabricated in the graphene layer(s) in proximity of the substance. Bent surface sections may be used to increase the field strength of radiation generated during the measurements.

The step of fabricating the structure may further comprise adding a field enhancing material, which is separated from the substance by the graphene layer(s).

Further, the structure may be fabricated such that both the graphene layer(s) and the field enhancing material each have a bent surface section in proximity of the enclosed substance.

The measurement step preferably comprises generating electromagnetic radiation and directing the electromagnetic radiation towards the substance.

The wavelength of the electromagnetic radiation preferably falls within a wavelength range from the ultraviolet through the visible to the infrared region where the electromagnetic radiation may excite the field enhancing material and/or the graphene layer(s) to generate secondary electromagnetic fields which increase the amplitude of the electromagnetic radiation inside the substance.

The field enhancing material may consist of or may comprise one or more of the following materials: metal (preferably gold), graphite, and $MoS_2$.

Alternatively or additionally, the measurement step may comprise the steps of: generating electromagnetic radiation in the visible and/or infrared range and directing said electromagnetic radiation towards the covered substance, and exciting the graphene layer to generate secondary fields which increase the amplitude of the radiation inside the substance.

The step of fabricating the structure preferably comprises the steps of: providing a carrier, depositing said substance on top of the carrier, and covering the carrier and the substance with said at least one graphene layer.

The carrier may consist of monoclinic silicate or may at least comprise a monoclinic silicate (mica) surface. In this case, the substance may be deposited on the monoclinic silicate surface of the carrier, and the substance may be covered by at least one graphene layer.

The step of fabricating the structure may also comprise placing the substance between two or more graphene layers.

Further, the step of fabricating the structure may comprise the steps of: providing a carrier consisting of or comprising a field enhancing material, said carrier having at least one hole capable of localizing the substance on the carrier; placing said at least one graphene layer on top of the carrier; and filling said substance into said hole wherein said at least one graphene layer separates the substance from the carrier.

Furthermore, the substance to be analyzed may comprise one or more of the following substances: single molecules, molecular self-assembled layers, a polymeric molecule, a substance which is thermally, chemically and/or mechanically instable, DNA (Deoxyribonucleic acid), RNA (Ribonucleic acid), a protein, a synthetic polynucleotide, a polypeptide.

The measurement step may include one or more of the following measurement procedures: Scanning Probe Technique, Raman spectroscopy, Infrared spectroscopy, Scanning Tunneling Microscopy, Scanning Tunneling Spectroscopy, Scanning Probe Microscopy, and Surface Enhanced Raman Spectroscopy.

The structure is preferably fabricated using a carrier consisting of or at least comprising one or more of the following materials: graphite, a substrate coated with one or more graphene layers, materials of the mica group, $MoS_2$, glass, plated gold, and a silicon wafer.

BRIEF DESCRIPTION OF THE DRAWINGS

In order that the manner in which the above-recited and other advantages of the invention are obtained will be readily understood, a more particular description of the invention briefly described above will be rendered by reference to specific embodiments thereof which are illustrated in the appended figures. Understanding that these figures depict only typical embodiments of the invention and are therefore not to be considered to be limiting of its scope, the invention will be described and explained with additional specificity and detail by the use of the accompanying drawings in which:

FIG. 1 shows in an exemplary fashion a contact mode SFM (SFM: scanning force microscopy) surface height image of ds-DNA (double-stranded DNA) replicas in graphene.

FIG. 2 shows in an exemplary fashion a sketch of the sample cross section marked in FIG. 1.

FIG. 3 shows in an exemplary fashion a tapping mode image of the area imaged in FIG. 1 recorded a few minutes after contact mode imaging, indicating no damage is done to ds-DNA during contact mode imaging.

FIG. 4 shows in an exemplary fashion a tapping mode SFM height image of ds-DNA replicas in graphene of different thickness (number of graphene layers indicated on the image). The heights of DNA molecules and their replicas in the graphene layer (s) are on the order of one nanometer as can be estimated from the SFM images.

DETAILED DESCRIPTION OF THE PREFERRED EMBODIMENTS

The preferred embodiments of the present invention will be best understood by reference to the drawings, wherein identical or comparable parts are designated by the same reference signs throughout.

It will be readily understood that the present invention, as generally described herein, could vary in a wide range. Thus, the following more detailed description of the exemplary embodiments of the present invention, is not intended to limit the scope of the invention, as claimed, but is merely representative of presently preferred embodiments of the invention.

FIGS. 1 to 4 show in an exemplary fashion a single to a few layers of graphene which are exfoliated mechanically onto a mica surface covered with double stranded (ds) vector DNA. It can be seen that the topography of the graphene layers replicates the underlying ds-DNA rings, as shown by scanning force microscopy (SFM) imaging in intermittent contact (also known as tapping) and contact modes.

Figure 5:
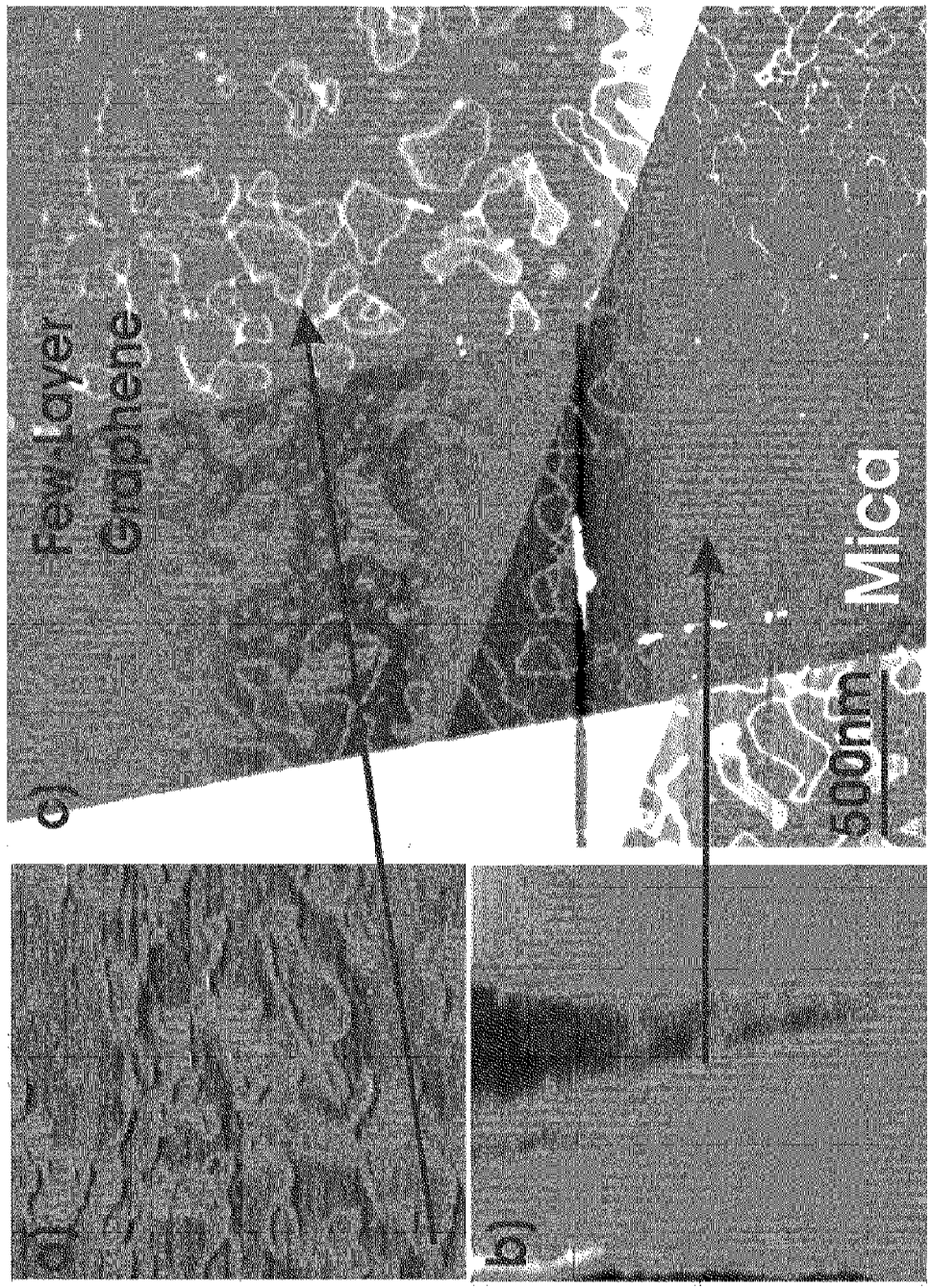
FIG. 5 shows in an exemplary fashion height images of samples with ds-DNA on a mica surface, coated and uncoated, respectively, with few layer graphene.

Attempts to image unprotected ds-DNA molecules on mica in contact mode under similar conditions destroy the molecules, proving that graphene may protect ds-DNA molecules on mica from wear and breakage. FIG. 5 shows in an exemplary fashion height images of samples with ds-DNA (including some contamination islands) on mica, coated and uncoated, respectively, with few layer graphene.

Sections a) and b) of FIG. 5 were taken in contact mode with the same scan parameters (~30 nN normal force). Section a) of FIG. 5 shows that ds-DNA coated with few layer graphene can be imaged reproducibly, while section b) of FIG. 5 shows that uncoated ds-DNA cannot be imaged reproducibly. Section c) of FIG. 5 shows an image taken subsequently in tapping mode. Arrows relate the sample areas recorded first in contact and then in tapping mode. It is apparent that contact mode imaging of ds-DNA not covered by graphenes destroyed the molecules, while ds-DNA covered by graphene remained intact. This implies the ability to perform profiling analysis of relatively soft and instable molecules even in contact mode SFM, which typically destructs macromolecules such as ds-DNA. The thickness of graphene is only 0.34 nm, allowing for precise profiling. In addition, both graphene and mica are optically highly transparent, i.e. the encapsulated molecules are accessible to optical excitation. Thus all methods described above, including TERS, will in principle still work on molecules encapsulated under graphene.

Moreover, graphene will protect the molecules against interactions with ambient, i.e. oxygen or water vapor, and thereby protect them from oxidative damage. In addition, graphene allows using a broad range of tip-surface distance control mechanisms including contact mode SFM, friction and shear force microscopy, as well as scanning tunneling microscopy (STM), the latter due to the high conductivity of graphene. Also a broad range of different spectroscopic techniques can be employed including scanning tunneling spectroscopy (STS) and conductive or Kelvin probe force microscopy.

Different exemplary structures comprising substances to be analyzed and protective graphene layers are shown in FIGS. 6-11.

Figure 6:
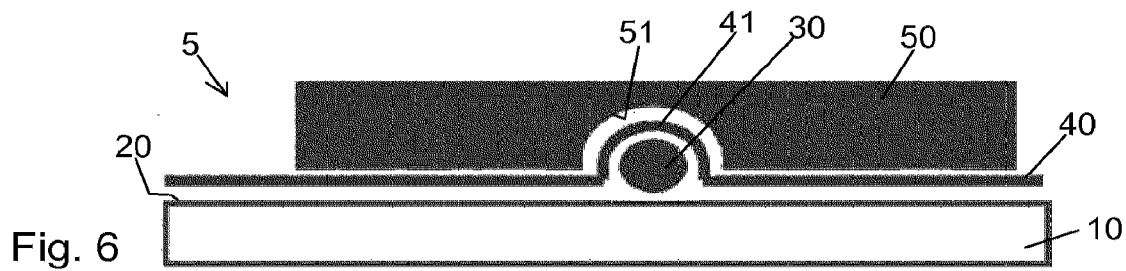
FIG. 6 shows a first exemplary embodiment of a structure comprising a substance to be analyzed, and at least one graphene layer.

FIG. 6 shows a first embodiment of a structure 5 comprising a carrier 10 having a mica surface 20. A substance 30, like DNA for instance, is deposited on the mica surface 20. Then, at least one graphene layer 40 is arranged on top. Further, a layer of a field enhancing material 50 is deposited on the surface of the graphene layer 40.

The field enhancing material 50 may be a plasmon active material, preferably gold or another conductor such as silver, graphite etc. The graphene layer 40 will protect the substance 30 from any chemical or physical interaction with the field enhancing material 50.

It can be seen in FIG. 6 that both the graphene layer 40 and the field enhancing material 50 have a bent surface section 41 and 51, respectively, both in proximity of the enclosed substance 30. The bent surface sections 41 and 51 form a cavity where the substance 30 is localized.

In order to analyze the substance 30, electromagnetic radiation may be generated e.g. for Raman or infrared spectroscopy. If the field enhancing material 50 is gold the preferred wavelength of the electromagnetic radiation ranges from 400 nm to 1.2 µm. The external radiation will excite the field enhancing material 50 to generate secondary fields which interfere with the external radiation such that the resulting electromagnetic field inside the substance 30 has an increased radiation amplitude.

Furthermore, depending on the wavelength of the external radiation, the graphene layer 40 may also exhibit plasmon activity in the ultraviolet with the plasmon tail even in the blue spectral region. Thus, the graphene layer 40 may also provide some enhancement of the measurement signal (e.g. a Raman signal) by increasing the radiation amplitude inside the substance 30.

In summary, the structure 5 of FIG. 6 allows avoiding any direct contact of the substance 30 (analyte) with the field enhancing material 50, while still keeping the substance 30 very close to the field enhancing material 50, which can therefore provide plasmon enhancement of the measured signal (e.g. a molecular Raman signal).

Figure 7:
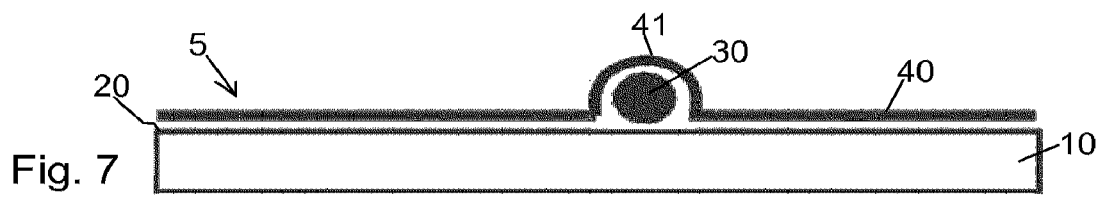
FIG. 7 shows a second exemplary embodiment of a structure comprising a substance to be analyzed, and at least one graphene layer.

FIG. 7 shows a second embodiment of a structure 5 comprising a carrier 10 having a mica surface 20. A substance 30, like DNA for instance, is deposited on the mica surface 20. Then, at least one graphene layer 40 is arranged on top. The graphene layer 40 will protect the substance 30 from chemical interaction with the external atmosphere.

The graphene layer 40 has a bent surface section 41 in proximity of the enclosed substance 30. The bent surface section 41 forms a cavity where the substance 30 is localized.

In order to analyze the substance 30, electromagnetic radiation may be generated e.g. for Raman or infrared spectroscopy. In order to excite the graphene layer 40 to generate secondary fields the preferred wavelength of the external electromagnetic radiation ranges from 1 nm to 1 mm. The secondary fields interfere with the external electromagnetic radiation such that an increased radiation amplitude is generated inside the substance 30.

In summary, the graphene layer 40 of FIG. 7 protects the substance 30 and simultaneously provides a field enhancing effect.

Figure 8:
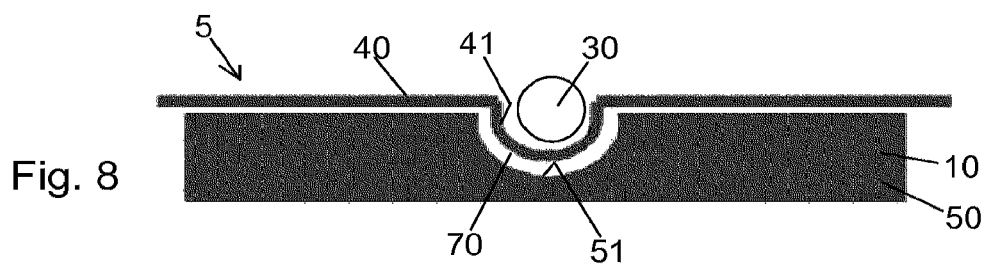
FIG. 8 shows a third exemplary embodiment of a structure comprising a substance to be analyzed, and at least one graphene layer.
Figure 9:
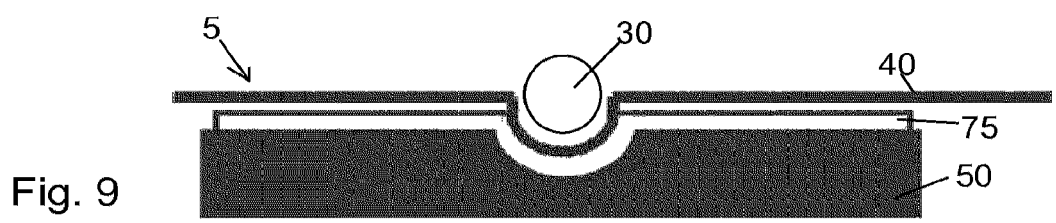
FIG. 9 shows a fourth exemplary embodiment of a structure comprising at least one graphene layer.

FIG. 8 shows a third embodiment of a structure 5 comprising a carrier 10 consisting of a field enhancing material 50 such as gold. The carrier 10 has at least one hole 70, the size of which being adapted to the volume of a substance to be analyzed. At least one graphene layer 40 is arranged on top of the field enhancing material 50. Then, the hole 70 is filled with the substance 30. The graphene layer 40 separates the substance 30 from the carrier 10.

The graphene layer 40 and the hole 70 have bent surface sections 41 and 51, respectively, in proximity of the carried substance 30. The bent surface sections form a cavity where the substance 30 is localized.

In order to analyze the substance 30, electromagnetic radiation may be generated e.g. for Raman or infrared spectroscopy. Depending on the wavelength of the electromagnetic radiation, the field enhancing material 50 and/or the graphene layer 40 will generate secondary fields which interfere with the external radiation such that an increased radiation amplitude is generated inside the substance 30.

In summary, the structure of FIG. 8 allows avoiding direct contact of the substance 30 (analyte) with the field enhancing material 50, while still keeping the substance 30 very close to the field enhancing material 50, which can therefore provide the plasmon enhancement with respect to the measured signal (e.g. a molecular Raman signal).

Referring again to FIG. 6, the structure 5 of FIG. 6 may be modified by removing the carrier 10. Then, the remaining structure consisting of the graphene layer 40, the substance 30, and the layer of a field enhancing material 50 may be used as a "SERS chip". On the one hand the protrusions created by the substance 30 will provide SERS active sites and on the other hand graphene will protect adsorbates from direct contact with the surface of the field enhancing material 50. However, after removal of the carrier 10 the graphene layer 40 might relax into a less stretched, i.e. plane conformation. In order to prevent the graphene layer 40 from relaxation, an adhesive layer 75 is preferably arranged between the graphene layer 40 and the field enhancing material 50. The adhesive layer 75 may also consist of a field enhancing material. The resulting structure 5 having an additional adhesive layer 75 is shown in an exemplary fashion in FIG. 9.

Figure 10:
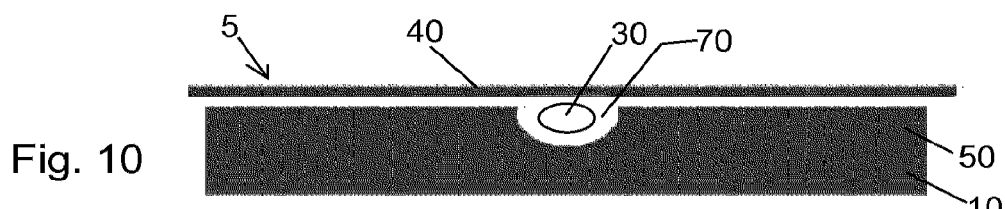
FIG. 10 shows a fifth exemplary embodiment of a structure comprising a substance to be analyzed, and at least one graphene layer.

FIG. 10 shows an exemplary embodiment of a structure 5 where a graphene layer 40 is relaxed into a planar conformation. Here, plasmon resonance properties of graphene may superpose with the plasmon resonance of the field enhancing material 50 of the carrier 10 in the area of the hole 70. The hole 70 may be a controlled quantum-sized defect in the carrier 10.

Figure 11:
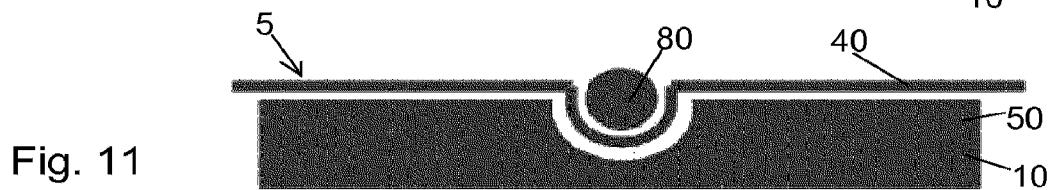
FIG. 11 shows a sixth exemplary embodiment of a structure comprising at least one graphene layer.

FIG. 11 shows an exemplary embodiment of a structure 5 where—in addition to the substance to be analyzed—particles 80 (e.g. nano-particles) of a plasmon active material are encapsulated in or carried by the graphene layer 40. The resulting structure 5 may be used to tune local surface plasmon activity for SERS applications. The substance to be analyzed is not shown in FIG. 11.

LITERATURE

[1] C. Lee et al., *Physica Status Solidi B-Basic Solid State Physics* 246, 2562 (2009).
[2] T. Eberlein et al., *Physical Review B* 77, 233406 (2008).
[3] J. R. Lombardi, R. L. Birke, *Journal of Physical Chemistry C* 112, 5605 (2008).

REFERENCE SIGNS 5 structure
10 carrier
20 surface
30 substance
40 graphene layer
41 bent surface section
50 field enhancing material
51 bent surface section 70 hole
75 adhesive layer
80 particle

The invention claimed is:

1. A method of analyzing a substance comprising the steps of:
fabricating a structure comprising said substance and at least one graphene layer;
carrying out at least one measurement step with respect to said structure; and
analyzing the measurement result of said measurement step to receive at least one analytical result concerning said substance,
wherein said step of fabricating said structure further comprises the step of adding a field enhancing material, wherein the at least one graphene layer separates the substance from the field enhancing material.

2. The method of claim 1 wherein at least one bent surface section is fabricated in the at least one graphene layer in proximity of the substance.

3. The method of claim 2 wherein said step of fabricating said structure further comprises the step of adding a field enhancing material, wherein the at least one graphene layer separates the substance from the field enhancing material.

4. The method of claim 3 wherein said structure is fabricated such that both, the at least one graphene layer and the field enhancing material, each have a bent surface section in proximity of the enclosed substance.

5. The method of claim 4 wherein said measurement step comprises the steps of generating electromagnetic radiation and directing said electromagnetic radiation towards the substance.

6. The method of claim 5 wherein the wavelength of said electromagnetic radiation falls within a wavelength range where the electromagnetic radiation may excite the field enhancing material or the graphene layer to generate secondary electromagnetic fields which increase the amplitude of the electromagnetic radiation inside the substance.

7. The method of claim 6 wherein said field enhancing material consists of or comprises one or more of the following materials: metal, graphite, and $MoS_2$.

8. The method of claim 1 wherein said step of carrying out said at least one measurement step comprises the steps of:
generating electromagnetic radiation in the ultraviolet-visible and/or infrared range and directing said electromagnetic radiation towards the covered substance, and
exciting the graphene layer to generate secondary fields which increase the amplitude of the radiation inside the substance.

9. The method of claim 1 wherein said step of fabricating said structure comprises the steps of:
providing a carrier;
depositing said substance on top of the carrier; and
covering the carrier and the substance with said at least one graphene layer.

10. The method of claim 9
wherein said carrier consists of monoclinic silicate or at least comprises a monoclinic silicate surface;
wherein the substance is deposited on the monoclinic silicate surface of the carrier; and
wherein the substance is covered by said at least one graphene layer.

11. The method of claim 1 wherein said step of fabricating said structure comprises the step of placing the substance between two or more graphene layers.

12. The method of claim 1 wherein said step of fabricating said structure comprises the steps of:
providing a carrier consisting of or comprising a field enhancing material, said carrier having at least one hole capable of localizing the substance on the carrier;
placing said at least one graphene layer on top of the carrier; and
filling said substance into said hole wherein said at least one graphene layer separates the substance from the carrier.

13. The method of claim 1 wherein the substance to be analyzed comprises one or more of the following substances: a single molecule, a plurality of single molecules, molecular self-assembled layers, a polymeric molecule, a plurality of polymeric molecules, a substance which is thermally, chemically or/and mechanically instable, DNA, RNA, a protein, a synthetic polynucleotide, a polypeptide.

14. The method of claim 1 wherein said at least one measurement step includes a Scanning Probe Technique and/or Raman Spectroscopy and/or Infrared Spectroscopy and/or Scanning Tunneling Microscopy and/or Scanning Tunneling Spectroscopy and/or Scanning Probe Microscopy and/or Surface Enhanced Raman Spectroscopy.

15. The method of claim 1 wherein the structure is fabricated using a carrier consisting of or at least comprising one or more of the following materials: graphite, a substrate coated with at least one graphene layer, mica material, $MoS_2$, glass, plated gold, and a silicon wafer.

* * * * *